United States Patent
Lin et al.

(10) Patent No.: US 9,075,092 B2
(45) Date of Patent: Jul. 7, 2015

(54) METHOD FOR OBTAINING ELECTRIC POWER INFORMATION

(71) Applicant: DELTA ELECTRONICS, INC., Kuei San, Taoyuan Hsien (TW)

(72) Inventors: Sheng-Hsien Lin, Taoyuan Hsien (TW); Chung-Ping Ku, Taoyuan Hsien (TW)

(73) Assignee: DELTA ELECTRONICS, INC., Taoyuan Hsien (TW)

( * ) Notice: Subject to any disclaimer, the term of this patent is extended or adjusted under 35 U.S.C. 154(b) by 251 days.

(21) Appl. No.: 13/712,096

(22) Filed: Dec. 12, 2012

(65) Prior Publication Data

US 2014/0028284 A1 Jan. 30, 2014

(30) Foreign Application Priority Data

Jul. 26, 2012 (TW) .............................. 101126973 A (51) Int. Cl.

| | |
|---|---|
| G01R 23/14 | (2006.01) |
| G01R 21/00 | (2006.01) |
| G01R 23/02 | (2006.01) |
| G01N 27/06 | (2006.01) |
| G06F 1/28 | (2006.01) |
| G01R 21/133 | (2006.01) |

(52) U.S. Cl.
CPC .............. *G01R 21/00* (2013.01); *G01R 23/02* (2013.01); *G01N 27/06* (2013.01); *G01R 21/133* (2013.01); *G06F 1/28* (2013.01)

(58) Field of Classification Search
CPC ......... G01R 31/34; G01R 23/02; G01R 31/40
USPC ................ 324/76.11, 76.39, 76.41, 119, 415, 324/764.01; 375/142
See application file for complete search history.

(56) References Cited

U.S. PATENT DOCUMENTS

| | | | | |
|---|---|---|---|---|
| 3,046,466 | A | 7/1962 | Tyrrell et al. | |
| 4,405,867 | A * | 9/1983 | Moakler et al. | 307/64 |
| 5,982,649 | A * | 11/1999 | Turner | 363/89 |
| 6,181,583 | B1 * | 1/2001 | Okui et al. | 363/45 |
| 6,366,864 | B1 | 4/2002 | Kulidjian et al. | |
| 6,828,771 | B1 | 12/2004 | Ghassemi | |
| 8,446,157 | B2 * | 5/2013 | Frojd | 324/681 |
| 2007/0157035 | A1 * | 7/2007 | Gumma et al. | 713/300 |
| 2007/0262647 | A1 * | 11/2007 | Luo et al. | 307/43 |
| 2008/0111526 | A1 * | 5/2008 | Shuey | 323/274 |
| 2010/0156377 | A1 * | 6/2010 | Siegler | 323/284 |
| 2011/0068811 | A1 | 3/2011 | Frojd | |
| 2011/0141770 | A1 * | 6/2011 | Wilson | 363/16 |
| 2012/0025806 | A1 * | 2/2012 | Chui et al. | 324/76.11 |
| 2012/0049808 | A1 | 3/2012 | Nakai | |
| 2012/0112735 | A1 | 5/2012 | Tokunaga | |
| 2012/0249091 | A1 * | 10/2012 | Chen et al. | 323/207 |

* cited by examiner

*Primary Examiner* — Minh N Tang
(74) *Attorney, Agent, or Firm* — Muncy, Geissler, Olds & Lowe, P.C.

(57) ABSTRACT

A method for obtaining electric power information is applied with a power supply and includes following steps of coupling the power supply to an AC power source; detecting a voltage of the AC power source to obtain a first voltage; detecting a frequency of the AC power source to obtain a first frequency; and estimating an electric power information of the power supply in accordance with the first voltage and the first frequency. The electric power information includes an input current, an input voltage or an input power outputted from the AC power source to the power supply.

10 Claims, 9 Drawing Sheets

FIG. 3D

METHOD FOR OBTAINING ELECTRIC POWER INFORMATION

CROSS REFERENCE TO RELATED APPLICATIONS

This Non-provisional application claims priority under 35 U.S.C. §119(a) on Patent Application No(s). 101126973 filed in Taiwan, Republic of China on Jul. 26, 2012, the entire contents of which are hereby incorporated by reference.

BACKGROUND OF THE INVENTION

1. Field of Invention

The present invention relates to a method for obtaining electric power information and, in particular, to a method for obtaining electric power information of a power supply.

2. Related Art

Power supplies have been widely applied to various electronic apparatuses, such as PC, notebook computers, or servers. The precision of the inputted current for the power supply of any electronic apparatus has become more and more critical. For example, the allowable range of the input current for the old generation electronic apparatus, which is equal to or larger than 3 A, is about 5%; however, the allowable range of the input current for the present electronic apparatus is about 3% only. This difference indicates that to precisely obtain the input current of the power supply is very important.

The existing method for obtaining the input current of the power supply is to provide a power monitoring chip between the power supply and the input terminal. However, this method may easily cause the damage of the power monitoring chip, which results in the malfunction of the electronic apparatus. Besides, this method also needs the additional optical coupler and isolated auxiliary power source, which increase the manufacturing cost. Another method is to estimate the input current of the power supply by the digital signal processor or single chip of the primary/secondary power factor correction (PFC) circuit. Unfortunately, this method can only directly estimate the real power instead of the input current of the power supply. In this method, an additional current transformer (CT) between the power supply and the input terminal is needed to obtain the input current of the power supply, which also increases the manufacturing cost.

Besides, the power supply must contain an X-capacitor for the safety consideration. Since the X-capacitor is connected with the AC power source in parallel, the accuracy of the capacitance of the X-capacitor can directly affect the precision of the input current of the power supply.

Therefore, it is an important subject to provide a method for obtaining electric power information can precisely estimate the input current of the power supply or the capacitance of the X-capacitor without the additional cost for the optical coupler, isolated auxiliary power source or current rectifier.

SUMMARY OF THE INVENTION

The present invention discloses a method for obtaining electric power information, which is applied with a power supply and includes following steps of: coupling the power supply to an AC power source; detecting a voltage of the AC power source to obtain a first voltage; detecting a frequency of the AC power source to obtain a first frequency; and estimating an electric power information of the power supply in accordance with the first voltage and the first frequency. The electric power information includes an input current, an input voltage or an input power outputted from the AC power source to the power supply.

In one embodiment of the invention, the method for obtaining electric power information further comprises steps of: detecting the voltage of the AC power source to obtain a second voltage; comparing the second voltage and the first voltage; and if the difference between the second voltage and the first voltage is greater than a threshold voltage, estimating and updating the electric power information in accordance with the second voltage.

In one embodiment of the invention, the method for obtaining electric power information further comprises steps of: detecting the frequency of the AC power source to obtain a second frequency; comparing the second frequency and the first frequency; and if the difference between the second frequency and the first frequency is greater than a threshold frequency, estimating and updating the electric power information in accordance with the second frequency.

In one embodiment of the invention, the method for obtaining electric power information further comprises steps of: detecting the voltage of the AC power source to obtain a reference voltage; detecting the frequency of the AC power source to obtain a reference frequency; detecting a current flowing through a capacitor of the power supply to obtain a reference current; and estimating a capacitance of the capacitor in accordance with the reference voltage, the reference frequency and the reference current.

In one embodiment of the invention, the input current is estimated according to a first current flowing through a capacitor of the power supply and a second current flowing through a power factor correction (PFC) circuit of the power supply.

In addition, the present invention also discloses a method for obtaining electric power information, which is applied with a power supply and includes steps of coupling the power supply to an AC power source; detecting a voltage of the AC power source to obtain a reference voltage; detecting a frequency of the AC power source to obtain a reference frequency; detecting a current flowing through a capacitor of the power supply to obtain a reference current; and estimating a capacitance of the capacitor and an electric power information of the power supply in accordance with the reference voltage, the reference frequency and the reference current. The electric power information includes an input current, an input voltage or an input power outputted from the AC power source to the power supply.

In one embodiment of the invention, the method for obtaining electric power information further comprises steps of detecting the voltage of the AC power source to obtain a first voltage; detecting the frequency of the AC power source to obtain a first frequency; and estimating and updating the electric power information in accordance with the first voltage, the first frequency and the capacitance of the capacitor.

In one embodiment of the invention, the method for obtaining electric power information further comprises steps of: detecting the voltage of the AC power source to obtain a second voltage; comparing the second voltage and the first voltage; and if the difference between the second voltage and the first voltage is greater than a threshold voltage, estimating and updating the electric power information in accordance with the second voltage.

In one embodiment of the invention, the method for obtaining electric power information further comprises steps of: detecting the frequency of the AC power source to obtain a second frequency; comparing the second frequency and the first frequency; and if the difference between the second frequency and the first frequency is greater than a threshold frequency, estimating and updating the electric power information in accordance with the second frequency.

In one embodiment of the invention, the input current is estimated and updated according to a first current flowing through the capacitor of the power supply and a second current flowing through a power factor correction (PFC) circuit of the power supply.

In summary, the method for obtaining electric power information of the invention can precisely estimate the input current of the power supply or the capacitance of the X-capacitor without the additional cost for the optical coupler, isolated auxiliary power source or current rectifier. Compared with the conventional art, the present invention has low manufacturing cost but high precision, and can be easily carried out by those skilled in the art, so that it has outstanding potential for marketing.

BRIEF DESCRIPTION OF THE DRAWINGS

The present invention will become more fully understood from the subsequent detailed description and accompanying drawings, which are given by way of illustration only, and thus are not limitative of the present invention, and wherein.

DETAILED DESCRIPTION OF THE INVENTION

The present invention will be apparent from the following detailed description, which proceeds with reference to the accompanying drawings, wherein the same references relate to the same elements.

Figure 1A:
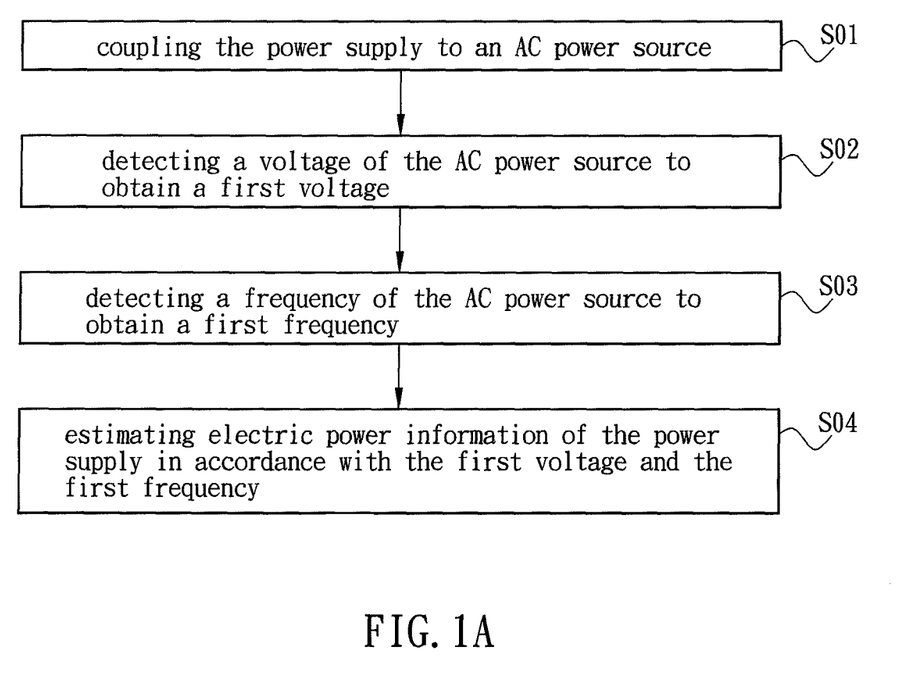
FIG. 1A is a flow chart of a method for obtaining electric power information according to a preferred embodiment of the invention.
Figure 2:
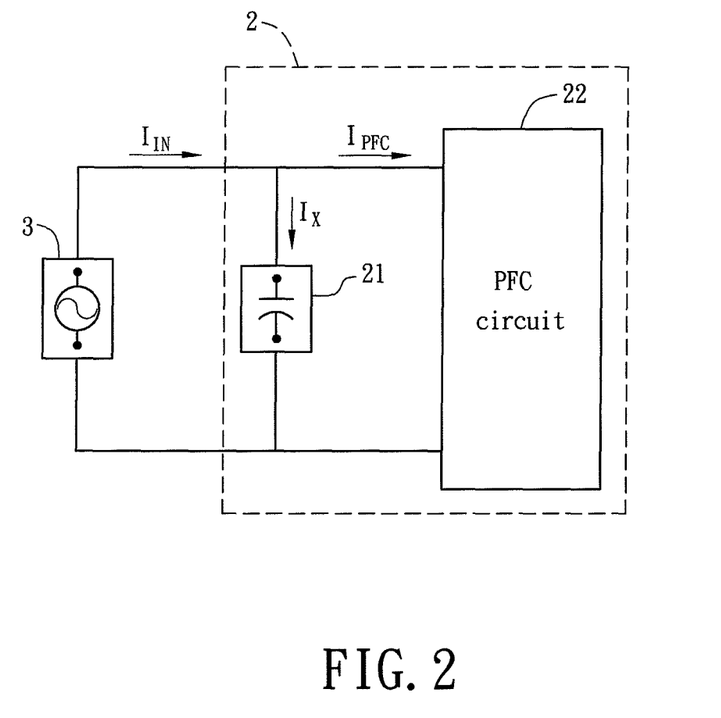
FIG. 2 is a schematic diagram showing the equivalent circuit of the hardware.

FIG. 1A is a flow chart of a method for obtaining electric power information according to a preferred embodiment of the invention, and FIG. 2 is a schematic diagram showing the equivalent circuit of the hardware. The method for obtaining electric power information of the embodiment, which is applied with a power supply 2, will be described hereinafter with reference FIG. 1A in view of FIG. 2.

The step S01 is to couple the power supply 2 to an AC power source 3. As shown in FIG. 2, the power supply 2 of this embodiment has a capacitor 21 (X-capacitor) and a power factor correction (PFC) circuit 22, and the capacitor 21 is connected with the AC power source in parallel.

The step S02 is to detect a voltage of the AC power source 3 to obtain a first voltage.

The step S03 is to detect a frequency of the AC power source 3 to obtain a first frequency.

In different embodiments, the steps S02 and S03 can use different detecting methods depending on the power supply. For example, a detecting unit or a single chip of the power supply can be used to perform the steps S02 and S03. Any approach that can obtain the first voltage and the first frequency is applicable, and this invention is not limited.

The step S04 is to estimate electric power information of the power supply in accordance with the first voltage and the first frequency. Herein, the electric power information includes an input current, an input voltage or an input power outputted from the AC power source 3 to the power supply 2.

After flowing to the power supply 2, the input current is divided into a first current and a second current. The first current is a current component flowing into the capacitor 21, and the second current is a current component flowing into the PFC circuit. The input current can be obtained according to the following equation (1) of "$(Mag(I_{IN}))^2=(I_{PFC})^2+(I_X)^2$" and equation (2) of "$I_X=V_{AC} \times F_{AC} \times 2 \times \pi \times C_X$". In the equation (1), $Mag(I_{IN})$ represents the vector value of the input current flowing into the power supply 2, $I_{PFC}$ represents the current value of the PFC circuit 22 (the current value of the second current), and $I_X$ represents the current value flowing into the capacitor 21 (the current value of the first current). In the equation (2), $I_X$ represents the current value flowing into the capacitor 21, $V_{AC}$ represents the voltage value of the AC power source 3, $F_{AC}$ represents the frequency value of the AC power source 3, and $C_X$ represents the capacitance value of the capacitor 21.

In this embodiment, assuming that $V_{AC}$ is the first voltage, $F_{AC}$ is the first frequency, and $C_X$ is the default value, $I_X$ can be calculated accordingly. Then, the calculated $I_X$ as well as $I_{PFC}$ (second current) obtained from the PFC circuit is substituted to the equation (1) so as to estimate $Mag(I_{IN})$, which is the desired input current.

To be noted, the above illustrated calculation is only for explanation, and in practice, the calculation is usually performed by the calculation unit or single chip of the power supply 2 instead of by human brain. Of course, it is possible to create an information table in advance, so that the electric power information can also be obtained by looking up the information table according to the first voltage and frequency.

Figure 1B:
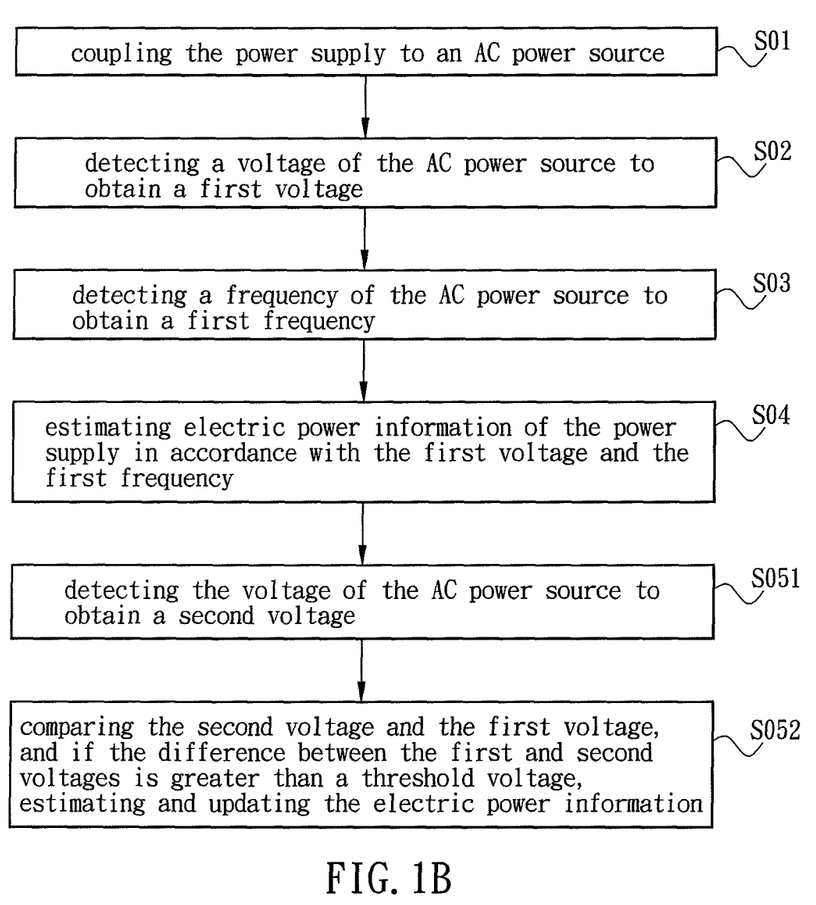
FIG. 1B is a flow chart of another method for obtaining electric power information according to the preferred embodiment of the invention.

FIG. 1B is a flow chart of another method for obtaining electric power information according to the preferred embodiment of the invention. The method of FIG. 1B is mostly the same as that of FIG. 1A, so the following description only illustrates the different parts and the similar parts will be omitted.

The step S051 is to detect the voltage of the AC power source to obtain a second voltage.

The step S052 is to compare the second voltage and the first voltage, and if the difference between the first and second voltages is greater than a threshold voltage, to estimate and update the electric power information. In other words, the estimation of the electric power information can be repeatedly estimated and updated. When the AC power source 3 has variation or the provided voltage is unstable, the power supply compares the real-time detected second voltage and the previously detected first voltage. If the voltage variation excesses the threshold voltage, the electric power information is estimated again and then updated. In this case, the second voltage rather than the first voltage is substituted into the equation (2) for calculation. On the contrary, if the voltage variation is smaller than the threshold voltage, the power supply determines that the electric power information is not needed to be recalculated and updated, and the previously estimated values are still suitable. In this embodiment, the threshold voltage is, for example, 4V; otherwise, in other embodiments, the threshold voltage can be different depending on the power supply. Besides, regarding to the same power supply, the threshold voltage may be adjustable based on the differences of the AC power source and load or other factors, and this invention is not limited.

Figure 1C:
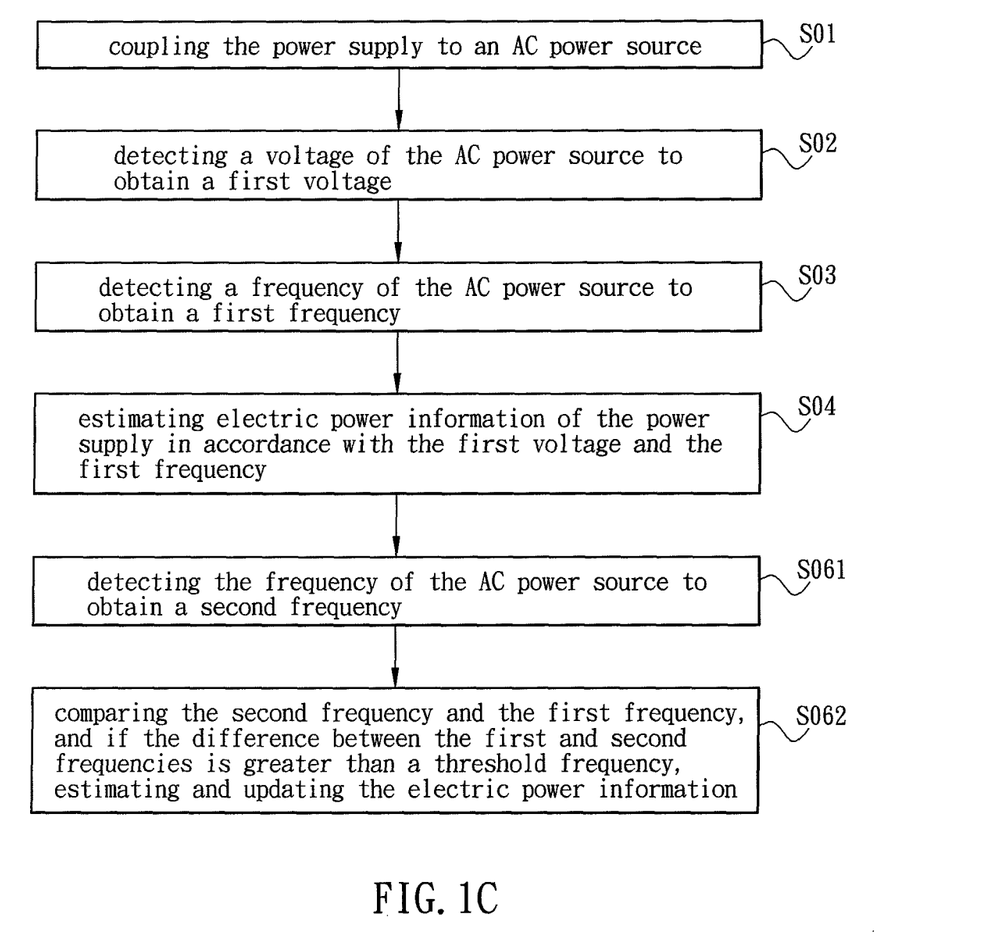
FIG. 1C is a flow chart of another method for obtaining electric power information according to the preferred embodiment of the invention.

FIG. 1C is a flow chart of another method for obtaining electric power information according to the preferred embodiment of the invention. The method of FIG. 1C is mostly the same as that of FIG. 1A, so the following description only illustrates the different parts and the similar parts will be omitted.

The step S061 is to detect the frequency of the AC power source to obtain a second frequency.

The step S062 is to compare the second frequency and the first frequency, and if the difference between the first and second frequencies is greater than a threshold frequency, to estimate and update the electric power information. In other words, the estimation of the electric power information can be repeatedly estimated and updated. When the AC power source 3 has variation or the provided frequency is unstable, the power supply compares the real-time detected second frequency and the previously detected first frequency. If the voltage variation excesses the threshold frequency, the electric power information is estimated again and then updated. In this case, the second frequency rather than the first frequency is substituted into the equation (2) for calculation. On the contrary, if the frequency variation is smaller than the threshold frequency, the power supply determines that the electric power information is not needed to be recalculated and updated, and the previously estimated values are still suitable. In this embodiment, the threshold frequency is, for example, 2 Hz; otherwise, in other embodiments, the threshold frequency can be different depending on the power supply. Besides, regarding to the same power supply, the threshold frequency may be adjustable based on the differences of the AC power source and load or other factors, and this invention is not limited.

Figure 1D:
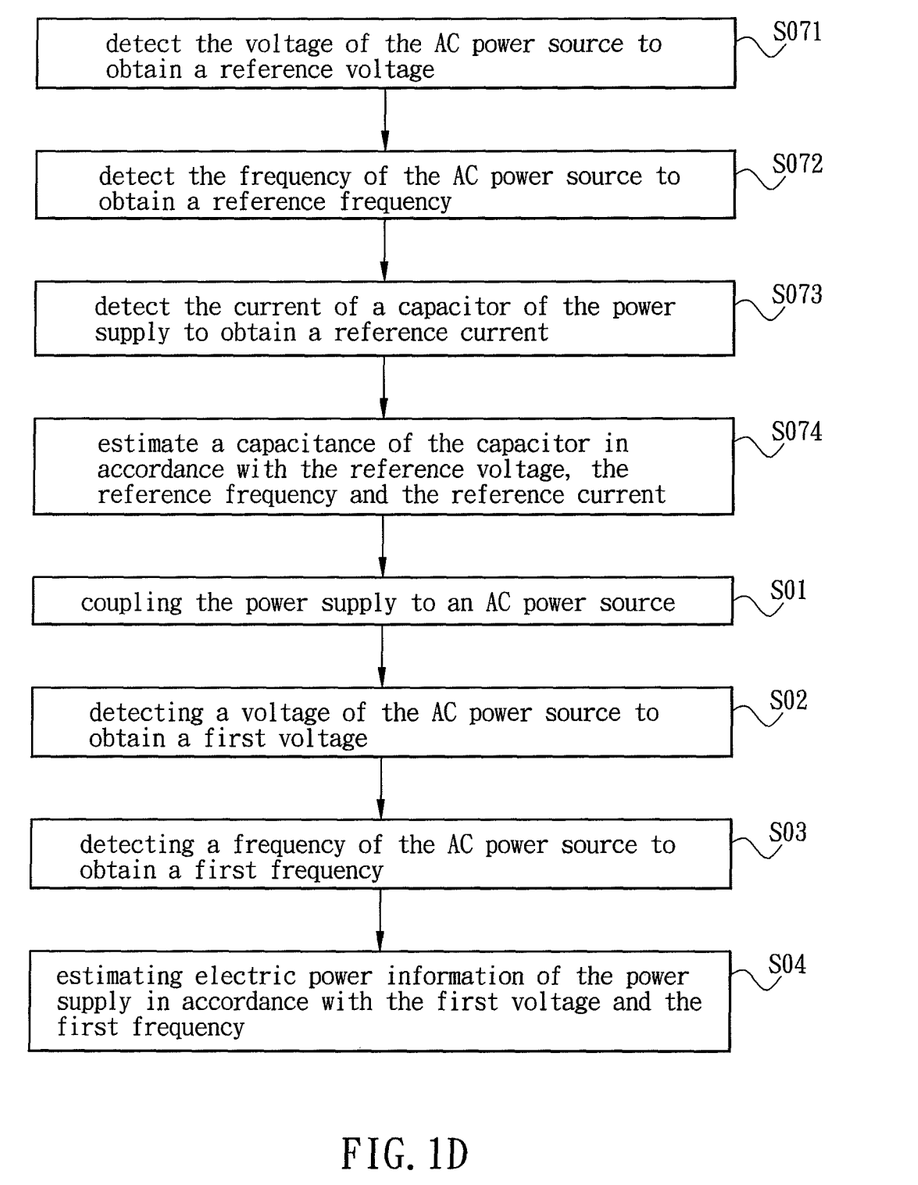
FIG. 1D is a flow chart of another method for obtaining electric power information according to the preferred embodiment of the invention.

FIG. 1D is a flow chart of another method for obtaining electric power information according to the preferred embodiment of the invention. The method of FIG. 1D is mostly the same as that of FIG. 1A, so the following description only illustrates the different parts and the similar parts will be omitted.

The step S071 is to detect the voltage of the AC power source to obtain a reference voltage.

The step S072 is to detect the frequency of the AC power source to obtain a reference frequency.

The step S073 is to detect the current of a capacitor of the power supply to obtain a reference current.

The step S074 is to estimate a capacitance of the capacitor in accordance with the reference voltage, the reference frequency and the reference current. In this embodiment, a calibration procedure will be performed before the step S01, which is to substitute the reference voltage, reference frequency and reference current into the equation (2) for calculating the capacitance of the capacitor 21. In more specific, different capacitors 21 may have some slightly variations during the manufacturing, so that the actual capacitance of each capacitor 21 may be different from that stated on the product label, which can interfere the precision of estimating the electric power information. Accordingly, the calibration procedure for the capacitance of the capacitor 21 can improve the precision of estimating the electric power information. The steps S071 to S074 are, for example, performed on the production line or before leaving the factory. The steps S01 to S04 are usually performed after the power supply is connected to the power source in use. To be noted, the steps S071 to S074 may also be performed after the power supply leaves the factory, and this invention is not limited.

Figure 3A:
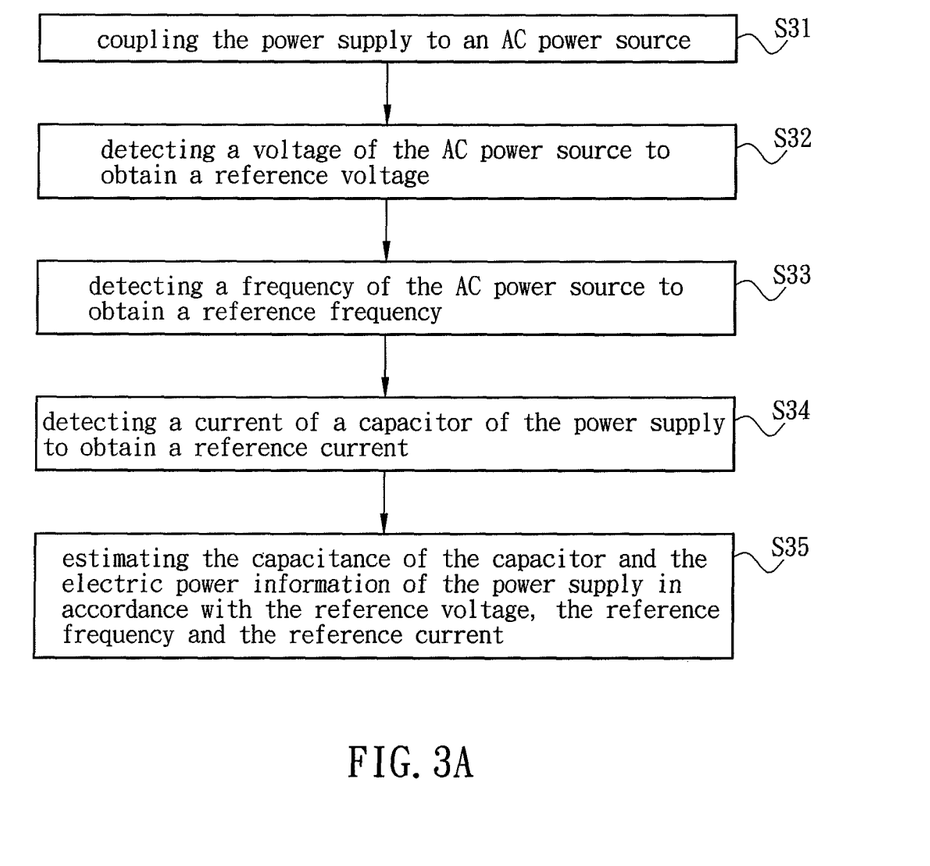
FIG. 3A is a flow chart of a method for obtaining electric power information according to another preferred embodiment of the invention.

FIG. 3A is a flow chart of another method for obtaining electric power information according to the preferred embodiment of the invention, and FIG. 2 is a schematic diagram showing the equivalent circuit of the hardware. The method for obtaining electric power information of this embodiment is applied with a power supply 2, which will be described hereinafter with reference to FIG. 3A in view of FIG. 2.

The step S31 is to couple the power supply 2 to an AC power source 3.

The step S32 is to detect a voltage of the AC power source 3 to obtain a reference voltage.

The step S33 is to detect a frequency of the AC power source 3 to obtain a reference frequency.

The step S34 is to detect a current of a capacitor 21 of the power supply 2 to obtain a reference current.

In different embodiments, the steps S32 to S34 can use different detecting methods depending on the power supply. For example, a detecting unit or a single chip of the power supply can be used to perform the steps S32 to S34. Any approach that can obtain the reference voltage, the reference frequency and the reference current is applicable, and this invention is not limited.

The step S35 is to estimate the capacitance of the capacitor and the electric power information of the power supply in accordance with the reference voltage, the reference frequency and the reference current. Herein, the electric power information includes an input current, an input voltage or an input power outputted from the AC power source 3 to the power supply 2.

For example, the capacitance of the capacitor 21 or the electric power information can be obtained according to the above-mentioned equation (1) and equation (2). In other words, the reference voltage, reference frequency and reference current are substituted into the equation (2), $V_{AC}$, $F_{AC}$ and $I_X$, for estimating the capacitance of the capacitor 21. Then, the reference current (the first current) and the second current flowing into the PFC circuit (obtained by the PFC circuit 22) are substituted into the equation (1), $I_X$ and $I_{PFC}$, for estimating the output current. To be noted, in other embodiments, the calibration procedure can be performed with only considering the capacitance of the capacitor 21 and without considering the input current.

Figure 3B:
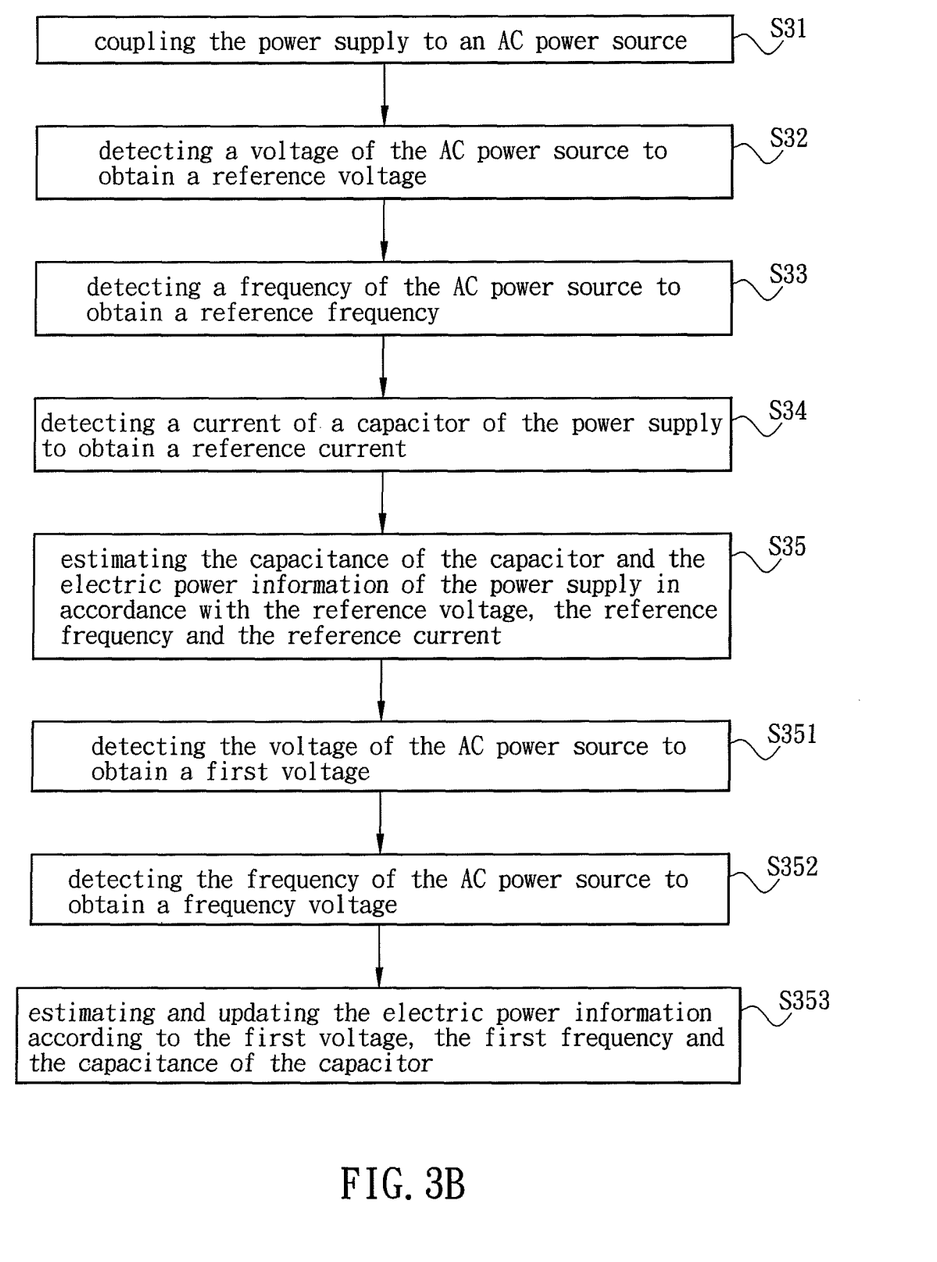
FIG. 3B is a flow chart of another method for obtaining electric power information according to another preferred embodiment of the invention.

FIG. 3B is a flow chart of another method for obtaining electric power information according to the preferred embodiment of the invention. The method of FIG. 3B is mostly the same as that of FIG. 3A, so the following description only illustrates the different parts and the similar parts will be omitted.

The step S351 is to detect the voltage of the AC power source to obtain a first voltage.

The step S352 is to detect the frequency of the AC power source to obtain a frequency voltage.

The step S353 is to estimate and update the electric power information according to the first voltage, the first frequency and the capacitance of the capacitor.

For example, the steps S31 to S35 can carry out the calibration procedure of the power supply on the production line or before leaving the factory, so that it is possible to obtain more precisely capacitance of the capacitor 21 or to also provide the default electric power information of the power supply. The steps S351 to S353 are usually performed after the power supply leaves the factory and are used for calculating and updating the electric power information.

To be noted, the above illustrated calculation is only for explanation, and in practice, the calculation is usually performed by the calculation unit or single chip of the power supply 2 instead of by human brain. Of course, it is possible to create an information table in advance, so that the electric power information can also be obtained by looking up the information table according to the first voltage and frequency.

Figure 3C:
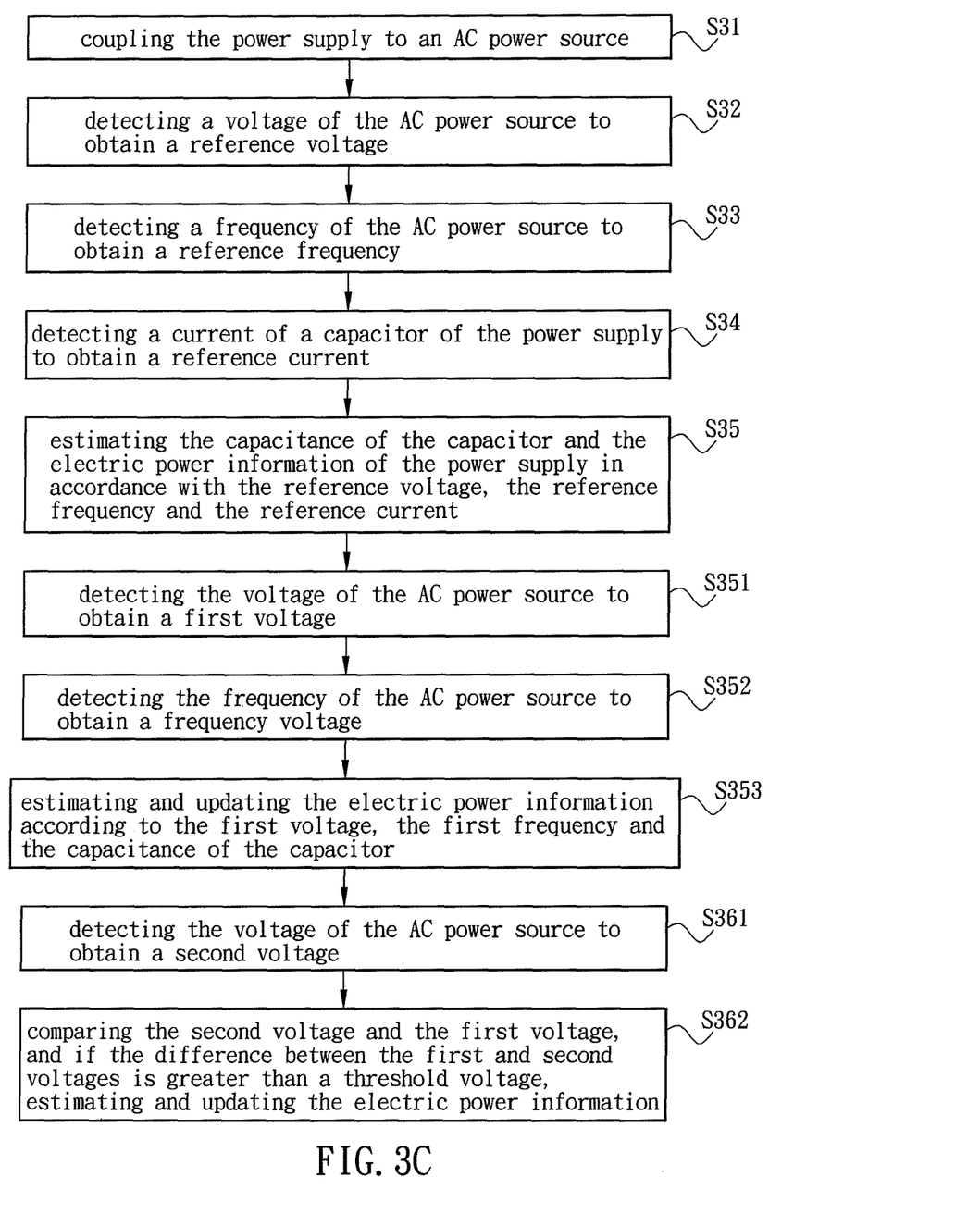
FIG. 3C is a flow chart of another method for obtaining electric power information according to another preferred embodiment of the invention.

FIG. 3C is a flow chart of another method for obtaining electric power information according to the preferred embodiment of the invention. The method of FIG. 3C is mostly the same as that of FIG. 3A, so the following description only illustrates the different parts and the similar parts will be omitted.

The step S361 is to detect the voltage of the AC power source 3 to obtain a second voltage.

The step S362 is to compare the second voltage and the first voltage, and if the difference between the first and second voltages is greater than a threshold voltage, to estimate and update the electric power information. In other words, the estimation of the electric power information can be repeatedly estimated and updated. When the AC power source 3 has variation or the provided voltage is unstable, the power supply compares the real-time detected second voltage and the previously detected first voltage. If the voltage variation excesses the threshold voltage, the electric power information is estimated again and then updated. In this case, the second voltage rather than the first voltage is substituted into the equation (2) for calculation. On the contrary, if the voltage variation is smaller than the threshold voltage, the power supply determines that the electric power information is not needed to be recalculated and updated, and the previously estimated values are still suitable. In this embodiment, the threshold voltage is, for example, 4V; otherwise, in other embodiments, the threshold voltage can be different depending on the power supply. Besides, regarding to the same power supply, the threshold voltage may be adjustable based on the differences of the AC power source and load or other factors, and this invention is not limited.

Figure 3D:
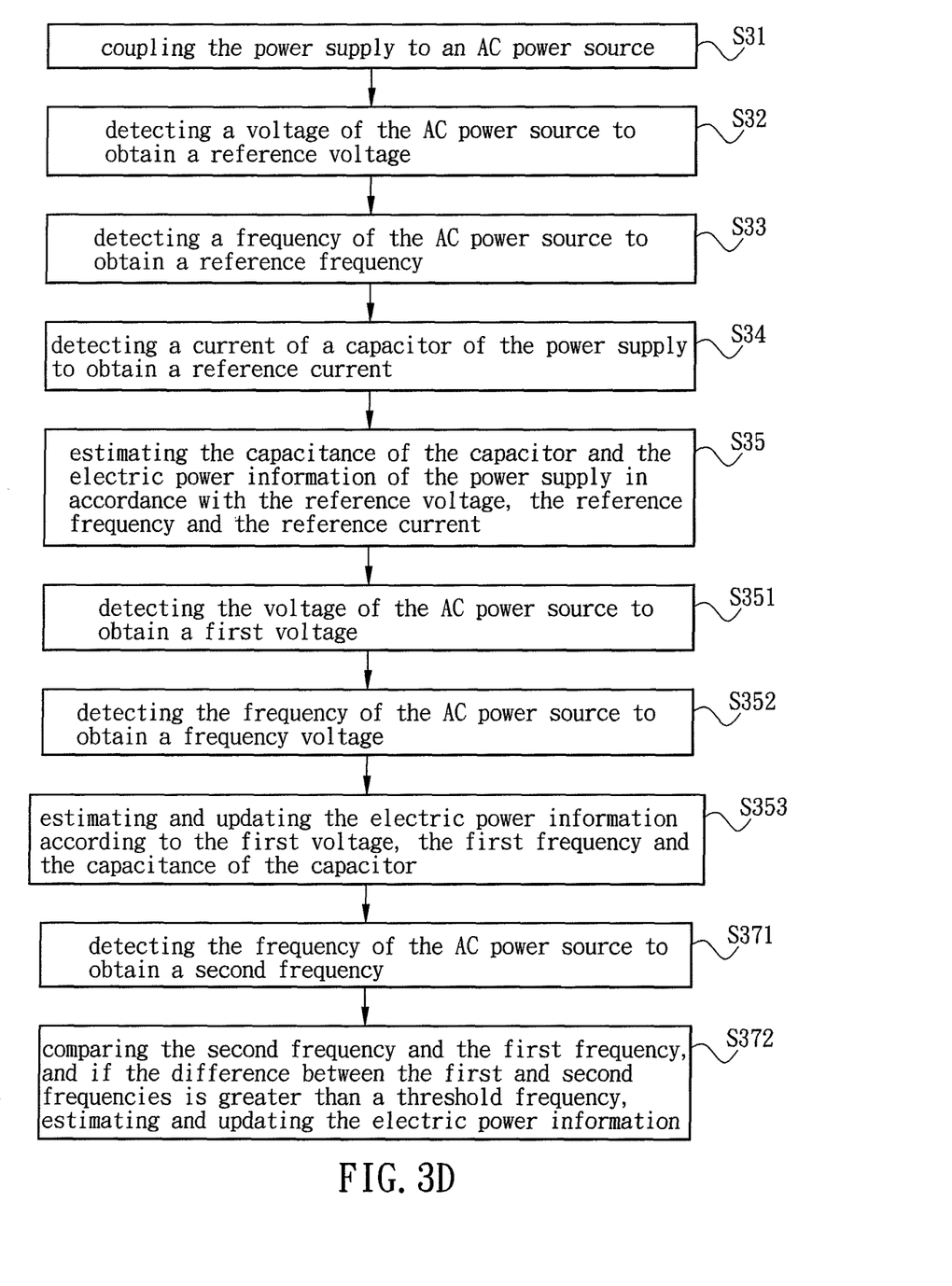
FIG. 3D is a flow chart of another method for obtaining electric power information according to another preferred embodiment of the invention.

FIG. 3D is a flow chart of another method for obtaining electric power information according to the preferred embodiment of the invention. The method of FIG. 3D is mostly the same as that of FIG. 3A, so the following description only illustrates the different parts and the similar parts will be omitted.

The step S371 is to detect the frequency of the AC power source to obtain a second frequency.

The step S372 is to compare the second frequency and the first frequency, and if the difference between the first and second frequencies is greater than a threshold frequency, to estimate and update the electric power information. In other words, the estimation of the electric power information can be repeatedly estimated and updated. When the AC power source 3 has variation or the provided frequency is unstable, the power supply compares the real-time detected second frequency and the previously detected first frequency. If the voltage variation excesses the threshold frequency, the electric power information is estimated again and then updated. In this case, the second frequency rather than the first frequency is substituted into the equation (2) for calculation. On the contrary, if the frequency variation is smaller than the threshold frequency, the power supply determines that the electric power information is not needed to be recalculated and updated, and the previously estimated values are still suitable. In this embodiment, the threshold frequency is, for example, 2 Hz; otherwise, in other embodiments, the threshold frequency can be different depending on the power supply. Besides, regarding to the same power supply, the threshold frequency may be adjustable based on the differences of the AC power source and load or other factors, and this invention is not limited.

In summary, the method for obtaining electric power information of the invention can precisely estimate the input current of the power supply or the capacitance of the X-capacitor without the additional cost for the optical coupler, isolated auxiliary power source or current rectifier. Compared with the conventional art, the present invention has low manufacturing cost but high precision, and can be easily carried out by those skilled in the art, so that it has outstanding potential for marketing.

Although the present invention has been described with reference to specific embodiments, this description is not meant to be construed in a limiting sense. Various modifications of the disclosed embodiments, as well as alternative embodiments, will be apparent to persons skilled in the art. It is, therefore, contemplated that the appended claims will cover all modifications that fall within the true scope of the present invention.

What is claimed is:

1. A method for obtaining electric power information, which is applied with a power supply, comprising steps of:
   coupling the power supply to an AC power source;
   detecting a voltage of the AC power source to obtain a first voltage;
   detecting a frequency of the AC power source to obtain a first frequency; and
   estimating an electric power information of the power supply in accordance with the first voltage and the first frequency;
   wherein, the electric power information is an input current outputted from the AC power source to the power supply.

2. The method of claim 1, further comprising steps of:
   detecting the voltage of the AC power source to obtain a second voltage;
   comparing the second voltage and the first voltage; and
   if the difference between the second voltage and the first voltage is greater than a threshold voltage, estimating and updating the electric power information in accordance with the second voltage.

3. The method of claim 1, further comprising steps of:
   detecting the frequency of the AC power source to obtain a second frequency;
   comparing the second frequency and the first frequency; and
   if the difference between the second frequency and the first frequency is greater than a threshold frequency, estimating and updating the electric power information in accordance with the second frequency.

4. The method of claim 1, further comprising steps of:
   detecting the voltage of the AC power source to obtain a reference voltage;
   detecting the frequency of the AC power source to obtain a reference frequency;
   detecting a current flowing through a capacitor of the power supply to obtain a reference current; and
   estimating a capacitance of the capacitor in accordance with the reference voltage, the reference frequency and the reference current.

5. The method of claim 1, Wherein the input current is estimated according to a first current flowing through a capacitor of the power supply and a second current flowing through a power factor correction (PFC) circuit of the power supply.

6. A method for obtaining electric power information, which is applied with a power supply, comprising steps of:
- coupling the power supply to an AC power source;
- detecting a voltage of the AC power source to obtain a reference voltage;
- detecting a frequency of the AC power source to obtain a reference frequency;
- detecting a current flowing through a capacitor of the power supply to obtain a reference current; and
- estimating a capacitance of the capacitor and an electric power information of the power supply in accordance with the reference voltage, the reference frequency and the reference current;
- wherein, the electric power information is an input current outputted from the AC power source to the power supply.

7. The method of claim 6, further comprising steps of:
- detecting the voltage of the AC power source to obtain a first voltage;
- detecting the frequency of the AC power source to obtain a first frequency; and
- estimating and updating the electric power information in accordance with the first voltage, the first frequency and the capacitance of the capacitor.

8. The method of claim 7, further comprising steps of:
- detecting the voltage of the AC power source to obtain a second voltage;
- comparing the second voltage and the first voltage; and
- if the difference between the second voltage and the first voltage is greater than a threshold voltage, estimating and updating the electric power information in accordance with the second voltage.

9. The method of claim 7, further comprising steps of:
- detecting the frequency of the AC power source to obtain a second frequency;
- comparing the second frequency and the first frequency; and
- if the difference between the second frequency and the first frequency is greater than a threshold frequency, estimating and updating the electric power information in accordance with the second frequency.

10. The method of claim 7, wherein the input current is estimated and updated according to a first current flowing through the capacitor of the power supply and a second current flowing through a power factor correction (PFC) circuit of the power supply.

* * * * *